(12) United States Patent
Wu

(10) Patent No.: US 9,375,449 B2
(45) Date of Patent: Jun. 28, 2016

(54) METAL ION NANOCLUSTERS

(75) Inventor: Chien-Chin Wu, Wilmington, DE (US)

(73) Assignee: LG Bionano, LLC, Wilmington, DE (US)

( * ) Notice: Subject to any disclaimer, the term of this patent is extended or adjusted under 35 U.S.C. 154(b) by 0 days.

(21) Appl. No.: 12/948,855

(22) Filed: Nov. 18, 2010

(65) Prior Publication Data

US 2012/0093898 A1    Apr. 19, 2012

(30) Foreign Application Priority Data

Oct. 19, 2010    (CN) .......................... 2010 1 0516328

(51) Int. Cl.

| A61K 33/26 | (2006.01) |
|---|---|
| A61K 9/00 | (2006.01) |
| A61K 33/32 | (2006.01) |
| A61K 31/30 | (2006.01) |
| A61K 31/295 | (2006.01) |
| A61K 31/194 | (2006.01) |
| A61K 33/00 | (2006.01) |
| A61K 9/14 | (2006.01) |
| A61K 31/7032 | (2006.01) |
| A61K 33/06 | (2006.01) |
| A61K 31/315 | (2006.01) |
| A61K 31/7016 | (2006.01) |
| A61K 9/51 | (2006.01) |
| A61K 33/24 | (2006.01) |
| A61K 33/30 | (2006.01) |
| A61K 31/28 | (2006.01) |
| A23L 1/09 | (2006.01) |
| A23L 1/304 | (2006.01) |

(52) U.S. Cl.
CPC . *A61K 33/26* (2013.01); *A23L 1/09* (2013.01); *A23L 1/3045* (2013.01); *A61K 9/0056* (2013.01); *A61K 9/0095* (2013.01); *A61K 9/145* (2013.01); *A61K 9/5123* (2013.01); *A61K 31/194* (2013.01); *A61K 31/28* (2013.01); *A61K 31/295* (2013.01); *A61K 31/30* (2013.01); *A61K 31/315* (2013.01); *A61K 31/7016* (2013.01); *A61K 31/7032* (2013.01); *A61K 33/00* (2013.01); *A61K 33/06* (2013.01); *A61K 33/24* (2013.01); *A61K 33/30* (2013.01); *A61K 33/32* (2013.01)

(58) Field of Classification Search
None
See application file for complete search history.

(56) References Cited

U.S. PATENT DOCUMENTS

| 3,892,851 | A | * | 7/1975 | Hinkel, Jr. ..................... 424/690 |
|---|---|---|---|---|
| 4,058,621 | A | * | 11/1977 | Hill ................................ 514/502 |
| 4,786,510 | A | * | 11/1988 | Nakel et al. ..................... 426/74 |
| 4,786,518 | A | * | 11/1988 | Nakel et al. .................... 426/531 |
| 5,213,788 | A | * | 5/1993 | Ranney ........................ 424/9.322 |
| 6,342,257 | B1 | * | 1/2002 | Jacobson et al. ................. 426/74 |
| 6,599,498 | B1 | | 7/2003 | Groman et al. |
| 2003/0232084 | A1 | | 12/2003 | Groman et al. |
| 2005/0032743 | A1 | | 2/2005 | Miljkovic |
| 2005/0037996 | A1 | | 2/2005 | Beck et al. |
| 2006/0199972 | A1 | | 9/2006 | Johnson et al. |
| 2006/0293220 | A1 | | 12/2006 | Holt |
| 2007/0161600 | A1 | | 7/2007 | Helenek et al. |
| 2008/0167266 | A1 | * | 7/2008 | Justus .............................. 514/53 |
| 2008/0176941 | A1 | * | 7/2008 | Xiao et al. ..................... 514/502 |
| 2009/0035385 | A1 | * | 2/2009 | Bortz ............................. 424/604 |
| 2010/0009901 | A1 | * | 1/2010 | Rabovsky et al. ................ 514/6 |

FOREIGN PATENT DOCUMENTS

| AU | 2009202295 | | 7/2009 |
|---|---|---|---|
| CN | 1097989 A | | 2/1995 |
| CN | 101691410 A | | 4/2010 |
| DE | 19815744 A | | 10/1999 |
| IN | 187116 B | * | 2/2002 |
| JP | 2005-530863 A | | 10/2005 |
| WO | WO96/06101 | | 2/1996 |
| WO | WO-2006/025627 | | 3/2006 |
| WO | WO-2008-146710 | | 4/2008 |
| WO | WO 2010/007441 | | 1/2010 |

OTHER PUBLICATIONS

Kudasheva et al. Journal of Inorganic Biochemistry 2004 98:1757-1769.*
Abdelwahed et al. Advanced Drug Delivery Reviews 2006 58:1688-1713.*
Kohli Science. Dehli:Dorling Kindersley (India) Pvt. Ltd, 2009 35-37.*
Adhikari et al. Chemistry of Materials 2010 22:4364-4371.*
Ding et al. Royal Society of Chemistry 2014 4; 22651-22659.*
C. Holt et al.; "Ability of a beta casein phosphopeptide to modulate the precipitation of calcium phosphate by forming amorphous dicalcium phosphate nanoclusters"; Biochemical Journal, 314:1035-1039 (1996).
Doty, et al., "Extremely Stable Water-Soluble Ag Nanoparticles", Chem. Mater. 2005, 17, 4630-4635.
Tajmir-Riahi "Sugar Interaction with Magnesium Ion. Synthesis, Spectroscopic, and Structural Properties of Mg-Sugar Complexes Containing L-Arabinose" Journal of Inorganic Biochemistry vol. 22, pp. 55-64. 1984.
Siddiqui et al "Preparation and Characterization of Complexes of Aluminum-Sorbitol: Sorbitol-Citric Acid-Sorbitol-Dextrin and Citric Acid-Sucrose-Glucose and Dextrin" Pakistan Journal of Scientific and Industrial Research vol. 29, pp. 95-101. 1986.

(Continued)

*Primary Examiner* — Robert A Wax
*Assistant Examiner* — Caralynne Helm
(74) *Attorney, Agent, or Firm* — Cesari and McKenna LLP

(57) ABSTRACT

A composition containing a plurality of water-soluble nanoclusters ranging from 2 nm to 500 nm in diameter. Each of the nanoclusters contains one or more metal cations, one or more anions, and one or more water-soluble ligands. Also disclosed is a method of using the composition for treating various disorders such as anemia, heartburn, and diabetes.

22 Claims, No Drawings

(56) References Cited

OTHER PUBLICATIONS

Siddiqui et al "Chromium—Sorbitol—Dextrin and Citric Acid Complex" Proceedings of the Pakistan Academy of Sciences vol. 24, pp. 17-24. 1987.

Norkus et al "Speciation of Transition Metal Ion Complexes in Alkaline Solutions of Alditols 2. Cu(II) Complex Formation with D-Sorbitol" Chemija vol. 13, pp. 129-137. 2002.

Norkus et al "Cu(II) Complex Formation with Xylitol in Alkaline Solutions" Carbohydrate Research vol. 339, pp. 599-605. 2004.

* cited by examiner

METAL ION NANOCLUSTERS

CROSS-REFERENCE TO RELATED APPLICATIONS

Under 35 USC 119, this application claims the benefit of the Oct. 19, 2010 priority date of Chinese Application No. 201010516328.0, the contents of which are hereby incorporated by reference in their entirety.

BACKGROUND

It is known that certain metal ions are essential nutrients (including micronutrients). Deficiency of these ions leads to one or more disorders such as anemia (e.g., from iron deficiency), osteoporosis (e.g., from calcium deficiency), growth retardation (e.g., from zinc deficiency), and Keshan disease (e.g., from selenium deficiency). Oral, topical, or injection supplements are typically used to treat or prevent these disorders.

SUMMARY

In one aspect, the invention features a composition that includes a plurality of water-soluble nanoclusters ranging from 2 nm to 500 nm (e.g., 2-150 nm, 2-90 nm, 5-90 nm, or 2-50 nm) in diameter. Each of the nanoclusters contains one or more metal cations, one or more anions, and one or more nonpolymeric water-soluble ligands. The one or more nonpolymeric water-soluble ligands are selected from the group consisting of a monosaccharide, a hydrogenated monosaccharide, a disaccharide, a hydrogenated disaccharide, an oligosaccharide, and an oligosaccharide derivative. The molar ratio among the one or more metal cations, the one or more anions, and the one or more nonpolymeric water-soluble ligands is 1:0.1-9:0.1-10 (e.g., 1:0.5-3:1-4).

In another aspect, the invention features a composition including a plurality of water-soluble nanoclusters ranging from 2 nm to 500 nm (e.g., 2-150 nm, 2-90 nm, 5-90 nm, or 2-50 nm) in diameter. Each of the nanoclusters contains one or more metal cations, one or more anions, and one or more water-soluble ligands. The one or more metal cations are selected from the group consisting of cations of Cr, Al, Bi, Zn, Ba, Cu, Ti, Mg, Mn, Bi, Pt, Ca, Se, In, and Zr. The one or more water-soluble ligands are selected from the group consisting of a carbohydrate, a carbohydrate derivative, an amino acid, a polyether, polyol, and a polypeptide. The molar ratio among the one or more metal cations, the one or more anions, and the one or more water-soluble ligands is 1:0.1-9:0.1-10 (e.g., 1:0.5-3:1-4).

In still another aspect, the invention features an iron-containing composition including a plurality of water-soluble nanoclusters ranging from 2 nm to 500 nm (e.g., 2-150 nm, 2-90 nm, 5-90 nm, or 2-50 nm) in diameter. Each of the nanoclusters contains one or more iron cations, one or more anions, and one or more nonpolymeric water-soluble ligands. The one or more nonpolymeric water-soluble ligands are selected from the group consisting of xylitol, isomaltose, isomalt, arabinose, sorbitol, and fructooligosaccharide. The molar ratio among the one or more iron cations, the one or more anions, and the one or more nonpolymeric water-soluble ligands is 1:0.1-9:0.1-10 (e.g., 1:0.5-3:1-4).

As used herein, the term "carbohydrate" refers to monosaccharides (e.g., xylose, arabinose, glucose, mannose, fructose, galactose, and ribose), disaccharides (e.g., sucrose, lactose, maltose, and isomaltose), oligosaccharides (i.e., carbohydrates that are composed of 3-9 monosaccharide residues joined through glycosidic linkage, such as raffinose, melezitose, maltotriose, acarbose, stachyose, fructooligosaccharide, and galactooligosaccharides), and polysaccharides (e.g., dextrin and maltodextrin). The term "carbohydrate derivative" refers to a hydrogenated carbohydrate (e.g., xylitol, arabitol, mannitol, sorbitol, and isomalt) or an oxidized carbohydrate (e.g., gluconic acid, sodium gluconate, and gluconate ester). Similarly, the terms "monosaccharide derivative," "disaccharide derivative," and "oligosaccharide derivative" refer to their corresponding hydrogenated/oxidized derivatives.

The embodiments of the compositions described above may include one or more of the following features. The plurality of nanoclusters can have a molecular weight ranging from 3,500 to 1,000,000 Dalton (e.g., 6,000-300,000 Dalton or 10,000-120,000 Dalton). The one or more nonpolymeric water-soluble ligands are selected from the group consisting of xylitol, isomaltose, isomalt, arabinose, mannitol, sorbitol, and fructooligosaccharide. The one or more metal cations are selected from the group consisting of Fe(II) and Fe(III). The one or more metal cations are selected from the group consisting of Mg(II), Al(III), Ca(II), Cr(III), Cu(II), Zn(II), Mn(II), and Ti(IV). The one or more anions are selected from the group consisting of carbonate, citrate, malate, fumarate, tartrate, gluconate, oxalate, succinate, ascorbate, pyrophosphate, glycerophosphate, and lactate. The composition, either in dry form (e.g., powder or tablet), in semi-solid form (e.g. gel or cream), or in liquid form (e.g., beverage, syrup, lotion, or in an intravenous solution for total parenteral nutrition), can be a dietary supplement, a cosmetic composition (e.g., a skin or hair care product), or a pharmaceutical formulation. The composition can also be a food product. Examples include tea (e.g., a tea drink and the contents of a tea bag), salts, various sauces or dressings, candy, coffee, milk, baked food (such as bread, cake, and pastries), soft drinks, juice (e.g., a fruit extract and a juice drink), jelly, ice cream, yogurt, cereals, chocolates, and snack bars. The composition can be a transparent aqueous solution with a pH value not greater than 10 (e.g., pH=7-10).

In one particular embodiment, when the composition contains Fe(II) or Fe(III), the one or more nonpolymeric water-soluble ligands are selected from the group consisting of sorbitol, xylitol, mannitol, oligosacharrides, and isomalt, and the one or more anions are selected from the group consisting of carbonate, bicarbonate, phosphate, pyrophosphate, malate, glycerophosphate, and hydroxide; or the one or more nonpolymeric water-soluble ligands are sucrose; and the one or more anions are selected from the group consisting of carbonate, citrate, malate, fumarate, tartrate, oxalate, succinate, ascorbate, pyrophosphate, glycerophosphate, and lactate.

The invention also features a composition consisting essentially of the nanoclusters described above. The term "consisting essentially of" used herein limits the composition to the just-mentioned four ingredients and those that do not materially affect its basic and novel characteristics, i.e., the efficacy in treating one or more target conditions described herein (e.g., anemia, diabetes, obesity, osteoporosis, bacterial infections, skin disorder, and gastric reflux disease). An example of such a composition contains the just-mentioned nanoclusters and a pharmaceutically, cosmeceutically, or dietarily acceptable carrier. Another example is a soft chew composition containing the nanoclusters and various inactive additives (e.g., excipients, sweeteners, and artificial flavors).

Further, this invention features a method of making the above-described composition. The method includes providing a first transparent aqueous solution containing one or more water-soluble salts and one or more water-soluble ligands (e.g., natural ligands), and mixing the first transparent aqueous solution with one or more alkaline anions to form a second transparent aqueous solution having a pH value ranging between 3.5 and 11 (e.g., 6-10), so that a plurality of water-soluble nanoclusters ranging from 2 nm to 500 nm (e.g., 2-150 nm) in diameter are formed, each containing the one or more metal cations, the one or more alkaline anions, and the one or more water-soluble ligands. The one or more water-soluble salts include one or more metal cations (e.g., cations of metals from groups 2-15 of the periodic table that are essential nutrients). The one or more water-soluble ligands are selected from the group consisting of a carbohydrate, a carbohydrate derivative, an amino acid, a polyether, polyol, and a polypeptide. In the first transparent aqueous solution, the molar ratio between the one or more metal cations and the one or more water-soluble ligands is 1:0.1-10 (e.g., 1:0.5-3). In particular, the plurality of water-soluble nanoclusters as obtained by the method each has a molar ratio among the one or more metal cations, the one or more alkaline anions, and the one or more water-soluble ligands being 1:0.1-9:0.1-10 (e.g., 1:0.5-3:1-4).

The term "alkaline anion" refers to the anion of an alkaline compound such as sodium hydroxide, sodium carbonate, sodium bicarbonate, sodium citrate, sodium phosphate, sodium glycerophosphate, sodium pyrophosphate, etc. The term "naturally occurring ligands" or "natural ligands" refers to non-synthetic ligands that exist in nature, such as xylitol, sucrose, gluconic acid, sorbitol, and fructooligosaccharide.

In general, the above-described method can generate the water-soluble nanoclusters in less than 10 minutes. The method can further include isolating the plurality of water-soluble nanoclusters from the second transparent aqueous solution by filtrating the second transparent aqueous solution through a molecular membrane with a cut-off at 3,500-10,000 Dalton (e.g., 5,000 Dalton), or by adding a water soluble organic solvent such as alcohol into the second transparent aqueous solution to precipitate the plurality of water-soluble nanoclusters. The isolated nanoclusters may further be dried by conventional methods such as air dry, oven dry, or spray drying techniques.

The one or more water-soluble ligands used in the method are preferably naturally occurring carbohydrates such as a monosaccharide, a disaccharide, an oligosaccharide, and their derivatives. The use of naturally occurring ligands not only reduces manufacturing costs, eases burdens on the body, but is also ecofriendly.

In still another aspect, the invention features a method for treating iron deficiency disorders such as iron deficiency anemia by administering to a subject in need thereof an effective amount of the above-described composition containing iron nanoclusters.

In yet another aspect, the invention features a method for treating diabetes (e.g., type II diabetes) or lowering cholesterol levels by administering to a subject in need thereof an effective amount of the above-described composition containing chromium nanoclusters.

This invention further features a method for treating a gastric reflux disorder (e.g., heartburn or gastrointestinal ulcers) by administering to a subject in need thereof an effective amount of the above-described composition containing aluminum, magnesium, bismuth, and/or iron nanoclusters.

The nanocluster compositions described herein can also be used as a biological imaging agents (e.g., an iron-containing composition as an MRI contrast agent or barium-containing composition as an X-ray radiocontrast agent), eye care compositions (e.g., a Zn- or Cu-containing composition), anti-dandruff shampoos (e.g., a Zn-containing composition), antiperspirants or deodorants (e.g., an Al- or Cu-containing composition), anti-oxidants (e.g., a Se-containing composition), sunscreen (e.g., a Ti-containing composition), a total parenteral nutrition injection (e.g., a composition containing Mg, Zn, Fe, Cu, Mn, and Cr), or metabolism stimulants (e.g., an In-containing composition). As such, in a further aspect, the invention features a method of administering to a subject in need thereof an effective amount of the above-described composition to treat or prevent one or more of the following disorders or conditions: macular degeneration, sunburn, dandruff, and hyperhidrosis.

Also within the scope of this invention is a composition containing the composition described above for use in treating the above-described disorders or conditions, and the use of such a composition for the manufacture of a medicament for the just-mentioned treatment.

It has also been contemplated that the nanoclusters in the composition can be used as drug carriers. For example, the drugs can be coupled to the ligands of the nanoclusters via an ionic bond, a covalent bond, a hydrogen bond, or dipole interactions such as van der Waals force. As another example, the drug can be coupled to the metal cations of the nanoclusters.

The details of one or more embodiments of the invention are set forth in the description below. Other features, objects, and advantages of the invention will be apparent from the description and from the claims.

DETAILED DESCRIPTION

This invention is based, at least in part, on the unexpected findings that certain water-soluble natural ligands together with a metal cation and an anion can form nanoclusters stable both in solid form and in an aqueous solution over a broad range of pH values (e.g., between 2 and 12). For example, a composition of this invention, which contains iron sucrose citrate nanoclusters, is surprisingly a transparent solution stable at a pH of 6-10, and is thus suitable for both intravenous and intramuscular injection. In comparison, the commercially available iron sucrose injections have a pH of 10.5-11.1 and are therefore not suitable for intramuscular injection. The high pH of the commercial iron sucrose injections also seemingly causes hydrolysis of sucrose, resulting in a pH decline, which significantly reduces the product stability and thus shortens the shelf life of the product). As another example, a composition of this invention, which contains metal cations needed in a total parenteral nutrition injection (such as Mg, Zn, Fe, Cu, Mn, and Cr), is surprisingly a transparent solution stable at a pH of 4-10, and thus, in contrast to commercial electrolyte injections having a pH of 2, would not cause any tissue irritation.

In addition, unlike the corresponding free metal cations, the nanoclusters are unexpectedly palatable and compatible with various dietary supplements such as proteins (e.g., collagen), peptides, vitamins (e.g., vitamins A, D, and E), coenzymes (e.g., Q10), carotene, curcumin, sweeteners, caffeine, and the like. Other advantages of the composition described herein include its physiological or low osmolarity, transparent elegancy, and physical stability without sedimentation over a long period of time (e.g., a few years).

The ligands used for forming the nanoclusters are preferably natural organic ligands that are soluble in water and bind to metal cations strong enough to allow formation of aggregates on the scale of a few nanometers to a few hundred nanometers. Examples of suitable ligands include but are not limited to polyhydric alcohols such as sugar alcohol or polyhydric ethers as well as their carboxyalkyl-, amino-, amido-, or ester-derivatives, monosaccharides, disaccharides, polysaccharides (e.g., dextran and dextrin), hydrolyzed polysaccharide (e.g., hydrolyzed starch), oligosaccharides, and hydrolyzed oligosaccharides. More than one type of ligands can be used for producing one batch of nanoclusters.

The metal cations used for forming the nanoclusters are essential nutrients or cosmetically/pharmaceutically beneficial. Examples of the metal cations include those of chromium, aluminum, bismuth, zinc, barium, copper, titanium, magnesium, calcium, iron, selenium, manganese, indium, and a mixture thereof.

The anions used for forming the nanoclusters can either be inorganic anions (including chloride, hydroxide, nitrate, sulfate, bicarbonate, carbonate, phosphate, pyrophosphate, glycerophosphate, etc.) or organic anions (including citrate, malate, fumarate, tartrate, succinate, oxalate, gluconate, and the like). More than one type of anions can be used to produce one batch of nanoclusters.

The nanocluster-containing composition of this invention can be formed by various techniques. In one embodiment, they are produced by mixing a water soluble metal salt (e.g., ferric chloride), a ligand (e.g., xylitol), and an alkaline agent (e.g., sodium hydroxide) in water at a suitable temperature (e.g., 15-135° C. or preferably 65-95° C.) and pH value (e.g., pH 4-9 for most metal cations/ligands and pH 9-11.5 for forming magnesium- or sucrose-containing nanoclusters) for a selected process time (e.g., from a few minutes to a few hours). The nanoclusters thus formed typically range from 2 nm to 500 nm in diameter (or preferably 3-50 nm), determined by dynamic laser light scattering technique as described in B. J. Berne et al., "Dynamic Light Scattering," J. Wiley and Sons, Inc., New York, 1976; P. J. Freud et al., "A New Approach to particle Sizing by Dynamic Light Scattering," Microtrac, Inc.; and M. N. Trainer et al., "High-concentration submicron particle size distribution by dynamic light scattering," American Laboratory, July 1992. The aqueous solution containing these nanoclusters, because of their small size, appears transparent and elegant. To separate the nanoclusters from other components of the solution (e.g., unreacted free metal cations, anions, salts, and water-soluble ligands), techniques such as filtration (e.g., using a membrane with a selected molecular cut-off) and precipitation (e.g., using a water-soluble organic solvent such as ethanol) can be applied. The isolated nanoclusters can then be dried and milled to obtain a powdery solid. The nanocluster powder is thermally stable and can be used in a bakery formulation and in parenteral formulation. The powdery solid can also be redissolved in water to form a transparent solution, which is compatible with various beverages such as soft drinks, milk, and coffee.

The molar ratio between the metal cations, the anions, and the ligands in a composition of the invention can be 1:0.1-9:0.1-10, or any ratio in between. Typically, a subject (e.g., a human being or an animal) can be administered, once or periodically per day, with the composition in an amount that provides 0.03-2000 mg of a metal ion needed. For example, a single dose of the composition may provide 500-1500 mg of calcium, 0.04-0.2 mg of chromium, 0.5-5 mg of copper, 5-15 mg of iron, 150-350 mg of magnesium, 1-5 mg of magnesium, 0.025-0.15 mg of molybdenum, 0.01-0.1 mg of selenium, 0.01-1 mg of nickel, 0.01-1 mg of vanadium, and/or 5-20 mg of zinc.

The composition of this invention can be a dietary supplement, a cosmetic product, or a pharmaceutical formulation. As a dietary supplement, additional nutrients, such as minerals, amino acids, or herb extracts, may be included. As a cosmetic product, additional ingredients, such as humectants, whitening agents, anti-oxidants, or herb extracts, may be included. As a pharmaceutical formulation (in forms including but not limited to powders, capsules, tablets, emulsions and aqueous suspensions, dispersions and solutions), the composition of this invention can be used alone or in combination with pharmaceutically acceptable carriers. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an aqueous phase combined with emulsifying or suspending agents. If desired, certain sweetening, flavoring, or coloring agents can be added. The carrier in the pharmaceutical composition must be "acceptable" in the sense of being compatible with the active ingredient of the formulation (and preferably, capable of stabilizing it) and not deleterious to the subject to be treated. Examples of other carriers include colloidal silicon dioxide, magnesium stearate, sodium lauryl sulfate, and D&C Yellow #10.

The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, bread, donut, bagel, chocolates, snack bars, herbal extracts, dairy products (e.g., ice cream, and yogurt), soy bean product (e.g., tofu), and rice products.

The composition of this invention can be in various forms. When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets. As another example, it can be a soft chew composition that includes the nanoclusters described above, niacinamide, ascorbic acid, sodium ascorbate, folic acid, sugar, corn syrup, sucralose, soy lecithin, corn starch, glycerin, palm oil, xylitol, carrageenan, FD&C Yellow #6, FD&C Yellow #5, and natural and/or artificial flavors.

The composition of this invention can further contain one or more of epigallocatechin gallate (EGCG), CoQ10, lutein, lycopene, eicosapentaenoic acid, docosahexaenoic acid soy isoflavones, folic acid, and vitamin B12. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, xylitol, sacharin, aspartame, and sucralose. The composition can also contain amino acids, minerals, a flavor enhancer, or a coloring agent.

The composition of this invention, when containing iron, can be used to treat iron deficiency disorders such as iron deficiency anemia. Examples of this type of anemia include anemia associated with chronic blood loss, acute blood loss, pregnancy, childbirth, childhood development, psychomotor and cognitive development in children, breath holding spells, heavy uterine bleeding, menstruation, chronic recurrent hemoptysis, idiopathic pulmonary siderosis, chronic internal bleeding, gastrointestinal bleeding, parasitic infections, chronic kidney disease, dialysis, chemotherapy, surgery or acute trauma, chronic ingestion of alcohol, salicylates, steroids, non-steroidial anti-inflammatory agents, or erythropoiesis stimulating agents. In some aspects, the anemia is anemia of chronic disease, such as rheumatoid arthritis, cancer, Hodgkins leukemia, non-Hodgkins leukemia, cancer chemotherapy, inflammatory bowel disease, ulcerative colitis thyroiditis, hepatitis, systemic lupus erythematosus, polymyalgia rheumatica, scleroderma, mixed connective tissue disease, Sojgren's syndrome, congestive heart failure/cardiomyopathy, or idiopathic geriatric anemia. In still some embodiments, the anemia is due to impaired iron absorption or poor nutrition, such as anemia associated with Crohn's Disease, gastric surgery, ingestion of drug products that inhibit iron absorption, and chronic use of calcium.

In other embodiments, the composition of this invention, when containing chromium, can be used to treat diabetes (such as type II diabetes), lower cholesterol level, and treat obesity; when containing magnesium and aluminum/iron, can be used as antacids; or when containing Mg, Mn, Cr, Zn, and Cu ions, can be used as total parenteral nutrition injections.

The terms "treating" and "treatment" refer to the administration of an effective amount of a composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them.

The term "administration" covers oral, topical, or parenteral delivery to a subject a composition of the invention in any suitable form, e.g., food product, beverage, tablet, capsule, suspension, lotion, cream, gel, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. A sterile injectable composition, e.g., a sterile injectable aqueous or oleaginous suspension, can be formulated according to techniques known in the art using suitable dispersing or wetting agents (such as Tween 80) and suspending agents, if necessary. The sterile injectable preparation can also be a sterile injectable solution or suspension in a non-toxic parenterally acceptable diluent or solvent, for example, as a solution in 1,3-butanediol, propylene glycol, or glycerine. Among the acceptable vehicles and solvents that can be employed are xylitol, mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

An "effective amount" refers to a dose of the composition that is sufficient to provide a physical benefit (e.g., improving endurance), a mental benefit (e.g., alertness), an appearance benefit (e.g., anti-wrinkle), or a therapeutic benefit (e.g., lowering cholesterol levels, or reducing the risk of anemia). Both in vivo and in vitro studies can be conducted to determine optimal administration routes and doses.

The compositions described above can be preliminarily screened for their efficacy in treating the above-described conditions by in vitro assays and then confirmed by animal experiments and clinic trials. Other suitable analytical and biological assays are apparent to those of ordinary skill in the art. For example, the bioavailability of iron-containing nanoclusters can be measured by conducting pharmacokinetic studies and evaluated by the area under the curve in a plasma-drug concentration time curve with therapeutic end point verification such as hemoglobin value, ferritin concentration and so on.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Iron Xylitol Carbonate Nanoclusters 3000 g of xylitol and 700 g of ferric chloride hexahydrate were dissolved in 6000 g of water at 70° C. with stirring to produce a solution. The pH of the solution was raised to around 7 by adding rapidly in one portion a suitable amount of an aqueous solution containing 20 wt % of sodium carbonate. The pH of the solution was further raised to 9 by adding rapidly in one portion a suitable amount of an aqueous solution containing 20 wt % of sodium hydroxide. The temperature was maintained at 70° C. during the pH adjustment. In less than 10 minutes after the addition of NaOH, a transparent solution having a strong laser scattering characteristic was then obtained. This strong laser scattering property indicated formation of iron xylitol carbonate nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of about 25 wt %. The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

This iron xylitol solution can be mixed with vitamin B12 and folic acid and added into an aqueous solution which contained various proteins such as pig skin collagen and Colla Corii Asini (Donkey hide gelatin) as well as glycerol at 60° C. The resulting solution was cooled to 25° C. to form a palatable and transparent elastic film with no precipitation and metallic taste. The resulting material is suitable for anemia treatment.

Example 2

Iron Xylitol Hydroxide Nanoclusters 5472 g of xylitol and 5500 g of ferric chloride hexahydrate were dissolved in 2700 g of water at 85° C. with stirring to produce a solution. The pH of the solution was raised to 9 by adding rapidly a suitable amount of an aqueous solution containing 20 wt % of sodium hydroxide. In less than 10 minutes after the addition of NaOH, a transparent solution having a strong laser scattering characteristic was then obtained. This strong laser scattering property indicated formation of iron xylitol hydroxide nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of about 24.3 wt. %.

The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

Example 3

Iron Mannitol Hydroxide Nanoclusters 1500 g of mannitol and 856 g ferric chloride hexahydrate were dissolved in 3000 g of water at 85° C. with stirring to produce a solution. The pH of the solution was raised to around 9 by adding rapidly a suitable amount of an aqueous solution containing 20 wt % of sodium hydroxide. The temperature was maintained at 85° C. during the pH adjustment. Within 10 minutes after the addition of NaOH, a transparent solution having a strong laser scattering characteristic was then obtained. The solution was stirred until all the residue is dissolved. This strong laser scattering property indicated the formation of iron mannitol hydroxide nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of about 19.23 wt. %.

The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

Example 4

Iron Isomalt Hydroxide Nanoclusters 688 g of isomalt and 556 g of iron chloride hexahydrate were dissolved in 2000 g of water at 80° C. with stirring to produce a solution. The pH of the solution was raised to about 8.5 by adding rapidly a suitable amount of an aqueous solution containing 20 wt % of sodium hydroxide. In less than 10 minutes after the addition of sodium hydroxide, a transparent solution having a strong laser scattering characteristic was then obtained. This strong laser scattering property indicated formation of iron isomalt hydroxide nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of 17.6 wt. %.

The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

Example 5

Iron Sorbitol Carbonate Nanoclusters 1820 g of sorbitol and 2880 g ferric chloride hexahydrate were dissolved in 1000 g of water at 85° C. with stirring to produce a solution. The pH of the solution was raised to around 9 by adding rapidly a suitable amount of an aqueous solution containing 20 wt % of sodium carbonate. The temperature was maintained at 85° C. during the pH adjustment. Within 10 minutes after the addition of NaOH, a transparent solution having a strong laser scattering characteristic was then obtained. This strong laser scattering property indicated the formation of iron sorbitol Carbonate nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of about 22.1 wt. %.

The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

Example 6

Iron Sucrose Citrate Carbonate Nanoclusters 800 g of sucrose, 110 g of citric acid, and 278 g of ferric chloride hexahydrate were dissolved in 1200 g of water at 85° C. with stirring to produce a solution. The pH of the solution was raised to about 7 by adding rapidly in one portion a suitable amount of an aqueous solution containing 20 wt % of sodium carbonate. In less than 10 minutes after the addition of $Na_2CO_3$, a transparent solution having a strong laser scattering characteristic was then obtained. This strong laser scattering property indicated formation of iron citrate sucrose carbonate nanocluster. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of 15.7 wt. %.

The dry solid of nanoclusters was then redissolved in water to form a transparent solution with strong laser light scattering characteristics, indicating the reversibility of nanoclusters between solid and liquid forms and their thermal stability. The solution was tasteless with no metallic taste. The quick dissolution was also observed in 0.1 N HCl solution. In vitro iron bioavailability test was carried out according to a method as described in the article entitled "A Comparison of Physical Properties, Screening Procedures and Human Efficacy Trial For Predicting The Bioavailability of Commercial Elemental Iron Powders Used For Food Fortification" published by Sean R. Lynch, Thomas Bothwell, and the SUSTAIN (Sharing United States Technology to Aid in the Improvement of Nutrition) Task Force on Iron Powder in Int. J. Vitam. Nutr. Res., 77 (2), 2007, 107-124 and in the article entitled "A new tool to evaluate iron bioavailability" in Nutriview, 2008 March.

Example 7

Iron Copper Xylitol Gluconate Malate Hydroxide Nanoclusters 300 g of xylitol, 90 g of sodium gluconate, 90 gm malic acid, 10 g of cupric chloride dehydrate, and 278 g ferric chloride hexahydrate were dissolved in 600 g of water at 80° C. with stirring to produce a solution. The pH of the solution was raised to about 8 by adding rapidly in one portion a suitable amount of an aqueous solution containing 20 wt % of sodium hydroxide. In less than 10 minutes after the addition of Sodium Hydroxide, a transparent solution having a strong laser scattering characteristic was then obtained. This strong laser scattering property indicated formation of iron copper xylitol gluconate malate hydroxide nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of 18.87 wt. % and a copper content of 0.87 wt. %.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has red brown color without metallic taste.

Example 8

Magnesium Iron Copper Sorbitol Malate Carbonate Nanoclusters 500 g of sorbitol, 402 g of malic acid, 256 g of ferric chloride hexahydrate, 17 g of cupric chloride dehydrate, and 406 g of magnesium chloride hexahydrate were dissolved in 500 g of water at 80° C. with stirring to produce a solution. The pH of the solution was raised to about 7 by adding rapidly in one portion a suitable amount of an aqueous solution containing 20 wt % of sodium carbonate. In less than 10 minutes after the addition of $Na_2CO_3$, a transparent solution having a strong laser scattering characteristic was then obtained. This strong laser scattering property indicated formation of magnesium iron copper sorbitol malate carbonate nano clusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had an iron content of 15.4 wt. %, a magnesium content of 6.0 wt. %, a copper content of 0.82 wt. %.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has red brown color.

Example 9

Magnesium Iron Citrate Xylitol Hydroxide Nanoclusters 300 g of xylitol, 162.4 g of magnesium chloride hexahydrate, 111.2 g of ferric chloride hexahydrate, and 120 g of citric acid were dissolved in 400 g of water at 80° C. with stirring to produce a solution. The pH of the solution was raised to about 7 by adding rapidly in one portion a suitable amount of an aqueous solution containing 20 wt % of sodium hydroxide. In less than 10 minutes after the addition of sodium hydroxide, a transparent solution having a strong laser scattering characteristic was then obtained. This strong laser scattering property indicated formation of magnesium iron citrate xylitol hydroxide nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had a magnesium content of 6.3 wt. % and an iron content of 15.21 wt. %.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has red brown color.

Example 10

Magnesium Citrate Sorbitol Hydroxide Nanoclusters 722 g of sorbitol, 624 g of magnesium chloride hexahydrate, and 208 g of citric acid monohydrate were dissolved in 2020 g of water at 70° C. with stirring to produce a solution. The pH of the solution was raised to about 8 by adding an aqueous solution containing 20 wt % of sodium hydroxide. After the addition of NaOH, a colorless and transparent nanocluster solution having a strong laser scattering characteristic was then obtained instantly. This strong laser scattering property indicated formation of magnesium citrate sorbitol hydroxide nanoclusters. The nanoclusters were isolated by then adding ethanol into the solution to precipitate the magnesium citrate sorbitol hydroxide nanoclusters. Or the nanoclusters were isolated from the solvent and free ions through a cross-flow membrane filtration device using a membrane with a molecular weight cut-off at 3500 Dalton. The isolated nanoclusters were further dried in an oven at 80° C. to form a solid. Atomic absorption spectroscopy of the thus-obtained nanoclusters indicated that the nanoclusters had a magnesium content of 7.69 wt. %

Next, the nanocluster solid was collected and then redissolved in water to form a transparent solution with strong light scattering properties. This demonstrates that, unlike other magnesium hydroxide complex, the solid and liquid state of this magnesium nanocluster is reversible with good thermal stability. The resulting dry powder or the reconstituted solution had good acid neutralization capacity without metallic taste. This nanocluster solid or liquid can be mixed with food or pharmaceutical excipients to develop various nutraceutical or pharmaceutical products.

Example 11

Aluminum Citrate Sorbitol Hydroxide Nanoclusters 800 g of sorbitol, 600 g of aluminum chloride hexahydrate, and 250 g of citric acid monohydrate were dissolved in 3000 g of water at 70° C. with stirring to produce a solution. The pH of the solution was raised to about 8 by adding an aqueous solution containing 20 wt % of sodium hydroxide. After the addition of NaOH, a colorless and transparent nanocluster solution having a strong laser scattering characteristic was then obtained instantly. This strong laser scattering property indicated formation of magnesium citrate sorbitol hydroxide nanoclusters. The nanoclusters were further isolated by adding ethanol into the solution to precipitate the magnesium citrate sorbitol hydroxide nanoclusters. Or the nanoclusters were isolated from the solvent and free ions through a cross-flow membrane filtration device using a membrane with a molecular weight cut-off at 3500 Dalton. The isolated nanoclusters were further dried in an oven at 80° C. to form a solid.

Next, the nanocluster solid was collected and then redissolved in water to form a transparent solution with strong light scattering properties. This demonstrates that unlike other aluminum hydroxide complex the solid and liquid state of this magnesium nanocluster is reversible with good thermostability. The resulting dry powder or the reconstituted solution had good acid neutralization capacity without metallic taste. This nanocluster solid or liquid can be mixed with pharmaceutical excipients to develop various pharmaceutical products.

Example 12

Chromium Xylitol Hydroxide Nanoclusters 600 g of xylitol and 140 g of chromium (III) chloride hexahydrate were dissolved in 1200 g of water at 85° C. with stirring to produce a solution. The pH of the solution was raised to about 9 by adding rapidly in one portion a suitable amount of an aqueous solution containing 20 wt % of sodium hydroxide. Within 20 minutes a blue transparent solution having a strong laser scattering characteristic was then obtained. This strong laser scattering property indicated formation of chromium xylitol nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark red solid, which was further ground into a free flow powder. Atomic absorption spectroscopy of the thus-obtained nanoclusters indicated that the nanoclusters had a chromium content of 8.09 wt. %.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has blue color.

Example 13

Chromium Arabinose Carbonate Nanoclusters 30 g of arabinose and 7 g of chromium chloride hexahydrate were dissolved in 60 g of water at 75° C. with stirring to produce a solution. The pH of the solution was raised to about 4 by adding an aqueous solution containing 20 wt % of sodium carbonate. The pH of the solution was then further raised to 10 by rapidly in one portion a suitable amount of adding an aqueous solution containing 20 wt % of sodium hydroxide. The temperature was then raised to 90° C. In less than 10 minutes after the temperature reached 90° C., a blue transparent solution having a strong laser scattering characteristic was then obtained. This strong laser scattering property indicated formation of chromium arabinose nanoclusters. Ethanol was then added into the solution to precipitate the nanoclusters. Next, the precipitate was collected by filtration and then dried alone. Atomic absorption spectroscopy of the thus-obtained nanoclusters indicated that the nanoclusters had a chromium cont of 5.85%. Or the alcohol precipitate was mixed with mannitol and co-dried for further formulation use.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has blue color without metallic taste.

Example 14

Zinc Iron Copper Manganese Chromium Malate Citrate Xylitol Carbonate Nanoclusters 300 g of xylitol, 120 g of malic acid, 120 g of citric acid, 56 g of ferric chloride hexahydrate, 34 g of copper chloride dihydrate, 10 g of manganese chloride tetrahydrate, 136 g of zinc chloride, and 0.54 g of chromium chloride hexahydrate were dissolved in 320 g of water at 85° C. with stirring to produce a solution. The pH of the solution was raised to about 7 by adding rapidly in one portion a suitable amount of an aqueous solution containing 20 wt % of sodium carbonate. In less than 5 minutes after the addition of $Na_2CO_3$, a transparent solution having a strong laser scattering characteristic was then obtained. This strong laser scattering property indicated formation of zinc iron copper manganese chromium malate citrate xylitol carbonate nanoclusters. The nanoclusters were isolated from the solvent and free ions through cross-flow membrane filtration using a membrane with a molecular weight cut-off at 3500 Dalton. The isolated nanoclusters were further dried in an oven at 80° C. to form a dark green solid, which was further ground into a free flow powder for further formulation use, e.g., by mixing with various excipients. Atomic absorption spectroscopy of the thus-obtained nanoclusters indicated that the nanoclusters had a zinc content of 7.13 wt. %, an iron content of 3.8 wt. %, a copper content of 2.77 wt. %, a manganese content of 0.43 wt. %, and a chromium content of 0.023 wt. %.

The dry solid of nanoclusters was then redissolved in water to form a transparent solution with strong laser light scattering characteristics, indicating the reversibility of nanoclusters between solid and liquid forms and their thermal stability. The reconstituted nano-iron cluster has green color.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition comprising a plurality of water-soluble nanoclusters ranging from 2 nm to 500 nm in diameter, each of the nanoclusters containing one or more metal cations, one or more anions, and one or more water-soluble ligands, in which the one or more metal cations are selected from the group consisting of cations of Cr, Al, Bi, Zn, Ba, Cu, Ti, Mg, Mn, Ca, Se, In, Pt, and Zr; the one or more water-soluble ligands are selected from the group consisting of xylitol, isomaltose, isomalt, sorbitol, arabinose, mannitol, and fructooligosaccharide; and the molar ratio among the one or more metal cations, the one or more anions, and the one or more water-soluble ligands is 1:0.1-9:0.1-10 wherein the plurality of nanoclusters have a molecular weight ranging from 3,500 to 1,000,000 Dalton.

2. The composition of claim 1, wherein the one or more metal cations are selected from the group consisting of Mg(II), Al(III), Ca(II), Cr(III), Cu(II), Zn(II), Mn (II), and Ti(IV).

3. The composition of claim 1, wherein the plurality of nanoclusters have a molecular weight ranging from 3,500 to 300,000 Dalton.

4. The composition of claim 1, wherein the plurality of nanoclusters have a molecular weight ranging from 10,000 to 120,000 Dalton.

5. The composition of claim 1, wherein the composition is a food product.

6. The composition of claim 5, wherein the food is tea, soft drinks, juice, milk, coffee, jelly, ice cream, yogurt, cookies, cereals, bread, donut, bagel, chocolates, or snack bars.

7. The composition of claim 1, wherein the composition is a dietary supplement, a cosmetic composition, or a pharmaceutical formulation.

8. The composition of claim 1, wherein the composition is in dry form.

9. The composition of claim 1, wherein the composition is in liquid form.

10. The composition of claim 1, wherein the composition is a transparent aqueous solution having a pH value between 3.5 and 11.5.

11. The composition of claim 1, wherein the plurality of nanoclusters range from 2 nm to 150 nm in diameter.

12. A composition comprising a plurality of water-soluble nanoclusters ranging from 2 nm to 500 nm in diameter, each of the nanoclusters containing one or more metal cations, one or more anions, and one or more water-soluble ligands, in which the one or more metal cations are selected from the group consisting of Mg(II), Al(III), Ca(II), Cr(III), Cu(II), Zn(II), Mn (II), and Ti(IV); the one or more water-soluble ligands are selected from the group consisting of a carbohydrate, a carbohydrate derivative, an amino acid, a polyether, polyol, and a polypeptide; and the molar ratio among the one or more metal cations, the one or more anions, and the one or more water-soluble ligands is 1:0.1-9:0.1-10, wherein the plurality of nanoclusters have a molecular weight ranging from 3,500 to 1,000,000 Dalton.

13. The composition of claim 12, wherein the one or more water-soluble ligands are selected from the group consisting of xylitol, isomaltose, isomalt, sorbitol, arabinose, mannitol, and fructooligosaccharide.

14. The composition of claim 12, wherein the plurality of nanoclusters have a molecular weight ranging from 3,500 to 300,000 Dalton.

15. The composition of claim 12, wherein the plurality of nanoclusters have a molecular weight ranging from 10,000 to 120,000 Dalton.

16. The composition of claim 12, wherein the composition is a food product.

17. The composition of claim 16, wherein the food is tea, soft drinks, juice, milk, coffee, jelly, ice cream, yogurt, cookies, cereals, bread, donut, bagel, chocolates, or snack bars.

18. The composition of claim 12, wherein the composition is a dietary supplement, a cosmetic composition, or a pharmaceutical formulation.

19. The composition of claim 12, wherein the composition is in dry form.

20. The composition of claim 12, wherein the composition is in liquid form.

21. The composition of claim 12, wherein the composition is a transparent aqueous solution having a pH value between 3.5 and 11.5.

22. The composition of claim 12, wherein the plurality of nanoclusters range from 2 nm to 150 nm in diameter.

\* \* \* \* \*